(12) United States Patent
Kim et al.

(10) Patent No.: US 9,795,339 B2
(45) Date of Patent: Oct. 24, 2017

(54) SENSOR FOR MEASURING BIOMETRIC INFORMATION AND ITEM OF CLOTHING INCLUDING THE SAME

(71) Applicant: Industry-Academic Cooperation Foundation, Chosun University, Gwangju (KR)

(72) Inventors: Youn Tae Kim, Daejeon (KR); Jae Hyo Jung, Gwangju (KR); Ji Hoon Lee, Gwangju (KR); Si Ho Shin, Gwangju (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 0 days.

(21) Appl. No.: 14/879,124

(22) Filed: Oct. 9, 2015

(65) Prior Publication Data

US 2017/0007180 A1    Jan. 12, 2017

(30) Foreign Application Priority Data

Jul. 8, 2015    (KR) .................. 10-2015-0097230

(51) Int. Cl.
| | | |
|---|---|---|
| *H04Q 9/00* | (2006.01) | |
| *G08C 17/00* | (2006.01) | |
| *G11C 8/10* | (2006.01) | |
| *A61B 5/00* | (2006.01) | |
| *A61B 5/0488* | (2006.01) | |
| *A61B 5/024* | (2006.01) | |

(52) U.S. Cl.
CPC ............ *A61B 5/6801* (2013.01); *H04Q 9/00* (2013.01); *A61B 5/02444* (2013.01); *A61B 5/0488* (2013.01); *A61B 2562/162* (2013.01)

(58) Field of Classification Search
CPC ....................................................... A61B 5/00
See application file for complete search history.

(56) References Cited

U.S. PATENT DOCUMENTS

| | | | | |
|---|---|---|---|---|
| 5,458,123 | A * | 10/1995 | Unger | ................ A61B 5/0006 128/903 |
| 5,824,033 | A * | 10/1998 | Ferrari | ............... A61B 5/04087 607/142 |
| 8,739,397 | B2 | 6/2014 | Nagata et al. | |
| 2004/0040839 | A1* | 3/2004 | Yagi | ...................... C12Q 1/002 204/403.01 |
| 2005/0283061 | A1* | 12/2005 | Ryu | ................... A61B 5/04286 600/372 |

(Continued)

FOREIGN PATENT DOCUMENTS

| | | |
|---|---|---|
| JP | 5186506 B2 | 4/2013 |
| KR | 2009-0009645 A | 1/2009 |

(Continued)

*Primary Examiner* — Joseph Feild
*Assistant Examiner* — Pameshanand Mahase
(74) *Attorney, Agent, or Firm* — Renner, Otto, Boisselle & Sklar, LLP

(57) ABSTRACT

A sensor for measuring biometric information includes a biometric electrode sensing biometric information in a state in which the biometric electrode is in contact with a surface of the skin; and a signal line transmitting the sensed biometric information, wherein the biometric electrode is printed on an inner surface of an item of clothing that comes into contact with a human body.

11 Claims, 3 Drawing Sheets

(56) References Cited

U.S. PATENT DOCUMENTS

| | | | |
|---|---|---|---|
| 2009/0169870 A1* | 7/2009 | Zheng | C03C 17/007 |
| | | | 428/332 |
| 2010/0185076 A1 | 7/2010 | Jeong et al. | |
| 2011/0160601 A1* | 6/2011 | Wang | A61B 5/04085 |
| | | | 600/509 |
| 2013/0144131 A1* | 6/2013 | Wang | A61B 5/1477 |
| | | | 600/301 |
| 2015/0148646 A1 | 5/2015 | Park et al. | |
| 2016/0128632 A1* | 5/2016 | Wiebe | A61B 5/6804 |
| | | | 340/870.07 |

FOREIGN PATENT DOCUMENTS

| | | |
|---|---|---|
| KR | 2014-0121059 A | 10/2014 |
| KR | 10-2015-0061219 | 6/2015 |

* cited by examiner

SENSOR FOR MEASURING BIOMETRIC INFORMATION AND ITEM OF CLOTHING INCLUDING THE SAME

CROSS-REFERENCE TO RELATED APPLICATION

This application claims the benefit of Korean Patent Application No. 10-2015-0097230 filed on Jul. 8, 2015, with the Korean Intellectual Property Office, the disclosure of which is incorporated herein by reference.

BACKGROUND

The present disclosure relates to measurement of biometric information.

The present invention is derived from research conducted as part of the Institute for Information & Communications Technology Promotion(IITP)-Information Technology Research Center Program by the Ministry of Science, ICT and Future Planning [Project No.: 1711026714(R0992-15-1021), Research Title: Energy harvesting and wireless power transmission for wearable devices].

Generally, in order to accurately recognize patients' conditions and effectively provide a cure or in order to determine whether the general public is in poor health and take some precautions, or the like, techniques for accurately and effectively measuring various types of biometric information sensed in human bodies have been developed.

An electrocardiogram (ECG), typical biometric information, records an action current generated as heart muscles contract and expand according to a heartbeat, in which electrodes are placed on the skin of a body, an action current based on contraction of muscles of heart is measured, and the measured current data is shown as a graph.

In order to obtain the biometric information, generally, a one-time Ag/AgCl electrode is used on a body desired to be measured. However, the Ag/AgCl electrode may limit movement of a measurement target due to a lead wire (or a covered wire), cause user inconvenience in case of measurement over a long period of time or in a daily life, and cause an allergic reaction to the skin.

In addition, since the Ag/AgCl electrode uses a conductive hydrogel adhesive, adhesive strength of the electrode is degraded after used once on skin, making it impossible to use it repeatedly, and it is ineffective in terms of cost.

A biometric signal measuring apparatus including a biometric electrode is disclosed in Korean Patent Laid-Open Publication No. 2015-0061219 (Entitled "Biometric electrode and a biometric signal measuring apparatus including the same," dated Jun. 4, 2015).

RELATED ART DOCUMENT (Patent Document 1) Korean Patent Laid-Open Publication No. 2015-0061219

SUMMARY

An aspect of the present disclosure may provide a sensor for measuring biometric information and an item of clothing including the same, which do not interfere with movement of a target when a biometric signal of the target is measured, cause less feeling of irritation, and are advantageously used in conducting experiments for measuring a biometric signal over a long period of time.

An aspect of the present disclosure may also provide a sensor for measuring biometric information and an item of clothing including the same, which are able to measure signals at various body parts, eliminate the necessity to add or replace an electrode to measure a biometric signal to thus provide an advantage in terms of cost, and allow for washing to thus facilitate management (that is, the sensor and the item of clothing may be easily managed).

According to an aspect of the present disclosure, a sensor for measuring biometric information may include: a biometric electrode sensing biometric information in a state in which the biometric electrode is in contact with a surface of the skin; and a signal line transmitting the sensed biometric information, wherein the biometric electrode is printed on an inner surface of an item of clothing that comes into contact with a human body.

The biometric electrode may be formed by printing a mixture solution obtained by mixing a carbon nano-tube (CNT) dispersion to textile paint on an inner surface of the item of clothing.

The signal line may be formed by printing the mixture solution on an inner surface of the item of clothing, and the textile paint may be printed on a surface of the signal line.

The sensor may further include: a snap button provided at an end portion of the signal line; and a signal processing device having a detachable recess formed to be attached to or detached from the snap button, and receiving biometric information transmitted through the signal line.

The signal processing device may include: an amplifier amplifying the received biometric information; a filter filtering the amplified biometric information; and a communications module wirelessly transmitting the filtered biometric information outwardly.

According to another aspect of the present disclosure, an item of clothing may include: a sensor for measuring biometric information including a biometric electrode sensing biometric information in a state in which the biometric electrode is in contact with a surface of the skin and a signal line transmitting the sensed biometric information, wherein the biometric electrode is printed on an inner surface of the item of clothing that comes into contact with a human body.

The biometric electrode may be formed by printing a mixture solution obtained by mixing a carbon nano-tube (CNT) dispersion to textile paint on an inner surface of the item of clothing.

The signal line may be formed by printing the mixture solution on an inner surface of the item of clothing, and the textile paint may be printed on a surface of the signal line.

The sensor may further include: a snap button provided at an end portion of the signal line; and a signal processing device having a detachable recess formed to be attached to or detached from the snap button, and receiving biometric information transmitted through the signal line.

The signal processing device may include: an amplifier amplifying the received biometric information; a filter filtering the amplified biometric information; and a communications module wirelessly transmitting the filtered biometric information outwardly.

The item of clothing may be formed of a material having elasticity.

BRIEF DESCRIPTION OF DRAWINGS

The above and other aspects, features and advantages of the present disclosure will be more clearly understood from the following detailed description taken in conjunction with the accompanying drawings, in which.

DETAILED DESCRIPTION

Figure 1:
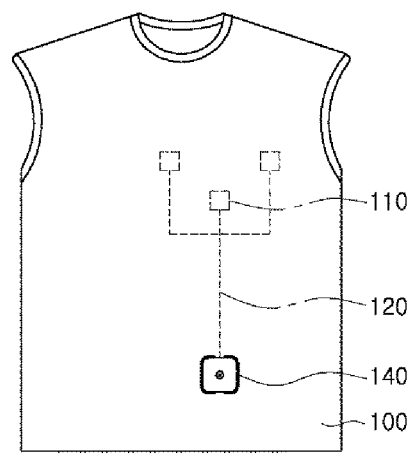
FIG. 1 is a view illustrating a sensor for measuring biometric information and an item of clothing including the same according to an exemplary embodiment of the present disclosure.

Hereinafter, exemplary embodiments of the present disclosure will be described in detail with reference to the accompanying drawings.

The disclosure may, however, be exemplified in many different forms and should not be construed as being limited to the specific embodiments set forth herein. Rather, these embodiments are provided so that this disclosure will be thorough and complete, and will fully convey the scope of the disclosure to those skilled in the art.

In the drawings, the shapes and dimensions of elements may be exaggerated for clarity, and the same reference numerals will be used throughout to designate the same or like elements.

Figure 2:
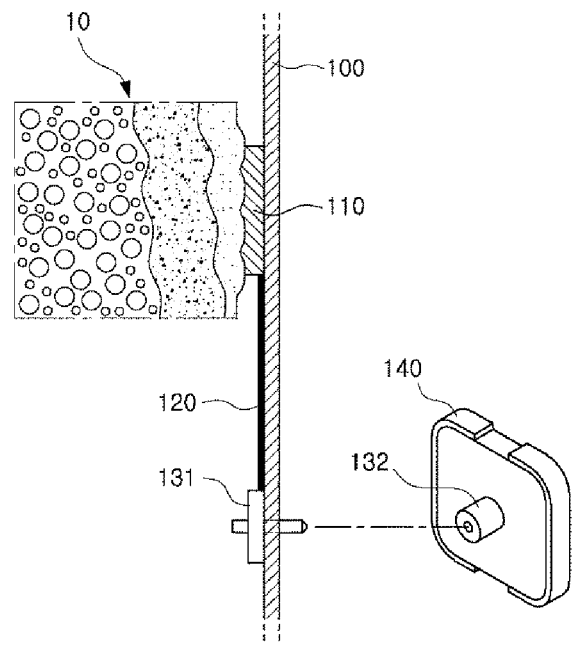
FIG. 2 is a cut side view illustrating the sensor for measuring biometric information and an item of clothing including the same according to an exemplary embodiment of the present disclosure.
Figure 3:
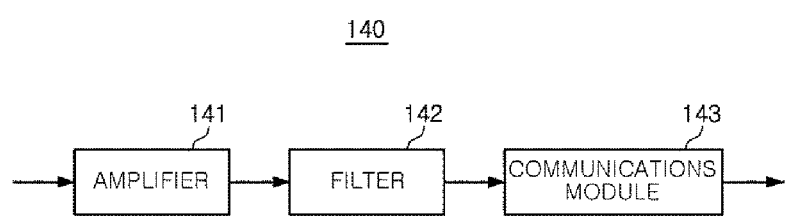
FIG. 3 is a block diagram of a signal processing device according to an exemplary embodiment of the present disclosure.

FIG. 1 is a view illustrating a sensor for measuring biometric information and an item of clothing including the same according to an exemplary embodiment of the present disclosure. FIG. 2 is a cut side view illustrating the sensor for measuring biometric information and an item of clothing including the same according to an exemplary embodiment of the present disclosure. FIG. 3 is a block diagram of a signal processing device according to an exemplary embodiment of the present disclosure.

As illustrated in FIGS. 1 and 2, the sensor for measuring biometric information according to an exemplary embodiment of the present disclosure may include a biometric electrode 110, a signal line 120, detachable members 131 and 132, and a signal processing device 140.

The biometric electrode 110, which may be brought into contact with a surface of the skin to sense biometric information, may be formed by directly printing a mixture solution obtained by mixing generally used textile paint and a carbon nano-tube (CNT) dispersion (liquid) on an inner surface of an item of clothing 100 in contact with the surface of the skin 10. The aforementioned textile paint is paint generally used to provide a pattern on cloth.

The aforementioned mixture solution may be prepared by mixing the CNT dispersion and the textile paint at an appropriate ratio. In order to prepare the CNT dispersion, 3.0 wt % of CNT and an isopropyl alcohol (IPA) solvent were mixed, stirred by a stirrer for 0.5 to 4 hours, aged for 24 hours, and a supernatant was subsequently removed using a centrifugal separator. Thereafter, a dispersing agent and a stabilizer were added. According to an exemplary embodiment, in order to enhance electric conductivity and reduce an allergy reaction, silver may be further added to the mixture solution. The aforementioned specific numerical values are merely illustrative to help understand the present disclosure, and the mixture solution may be realized by various other numerical values according to exemplary embodiments.

Biometric information to be sensed in the present disclosure may include an electrocardiogram (ECG) or an electromyogram (EMG).

As illustrated in FIG. 1, at least two biometric electrodes 110 may be printed on portions where measurement is to be performed. The biometric electrode 110 has a size of about 1.2 cm×1.2 cm, but the size of the biometric electrode 110 is not limited thereto. Also, the biometric electrode 110 may have various shapes such as a circular or quadrangular shape.

The signal line 120 serves to transmit biometric information sensed by the biometric electrode 110. In detail, the signal line 120 may be formed by printing a mixture solution obtained by mixing textile paint and a CNT dispersion from the biometric electrode 110 to a snap button 131 on an inner surface of the item of clothing 100 to form a connection line and subsequently drying the connection line at room temperature for two hours. According to exemplary embodiment, textile paint may be additionally printed on a surface of the signal line 120. This is to cancel noise that may be generated as the signal line 120 comes into direct contact with the skin.

The detachable members 131 and 132 include the snap button 131 and a detachable recess 132. The snap button 131 may be provided at an end portion of the signal line 120, and the detachable recess 132 may be formed in the signal processing device 140. The snap button 131 provided at the end portion of the signal line 120 and the detachable recess 132 formed in the signal processing device 140 may be detachable. Although a pair of detachable members 131 and 132 are illustrated in FIG. 1, two or more pairs of detachable members may be configured according to exemplary embodiments.

The signal processing device 140 is a module for processing a biometric signal received through the signal line 120.

As illustrated in FIG. 2, the detachable recess 132 may be formed in the signal processing device 140 and attached to or detached from the snap button 131 provided at the end portion of the signal line 120. Biometric information transmitted through the signal line 120 may be transmitted to the signal processing device 140 through the detachable recess 132.

In detail, as illustrated in FIG. 3, the signal processing device 140 may include an amplifier 141 amplifying the received biometric information, a filter 142 filtering the amplified biometric information, and a communications module 143 wirelessly transmitting the filtered biometric information outwardly. The communications module 143 may be a module for wireless communications such as Bluetooth, or the like.

The item of clothing 100 according to an exemplary embodiment of the present disclosure may be formed of a material having elasticity, such as polyester fiber, to allow the sensor for measuring biometric information to be tightly attached to a human body.

Figure 4A:
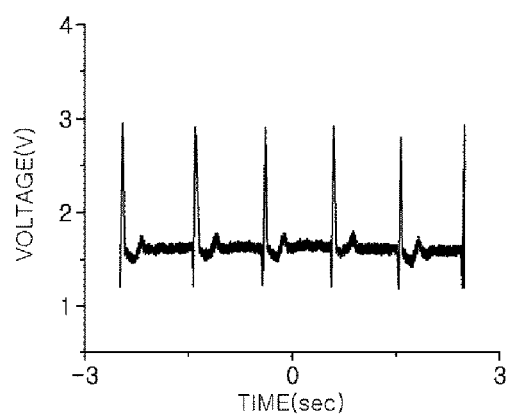
FIGS. 4A and 4B are graphs illustrating a comparison between biometric information measured through the related art Ag/AgCl electrode and biometric information measured by using a biometric electrode according to an exemplary embodiment of the present disclosure.
Figure 4B:
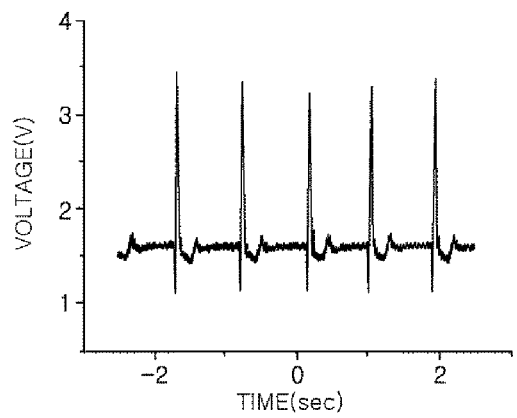

FIGS. 4A and 4B are graphs illustrating a comparison between biometric information measured through the related art Ag/AgCl electrode and biometric information measured by using a biometric electrode according to an exemplary embodiment of the present disclosure.

Specifically, in FIG. 4A, illustrates biometric information measured using the biometric electrode according to an exemplary embodiment of the present disclosure, and FIG.

4B illustrates biometric information measured through the related art Ag/AgCl electrode.

As illustrated in FIGS. 4A and 4B, it can be seen that the biometric information measured using the biometric electrode according to an exemplary embodiment of the present disclosure is not significantly different to the biometric information measured through the related art Ag/AgCl electrode. That is, the present disclosure may be compatible with an existing biometric measurement device, without affecting the quality of biometric information.

As set forth above, according to an exemplary embodiment of the present disclosure, since the biometric electrode formed of a mixture solution obtained by mixing a CNT dispersion to textile paint is printed on an inner surface of the item of clothing which come into contact with a human body so as to be used, it does not interfere with movement of a target when a biometric signal of the target is measured, causes less feeling of irritation, may be more tightly attached to a curved human body, and is advantageously used in conducting experiments for measuring a biometric signal over a long period of time.

In addition, according to an exemplary embodiment of the present disclosure, signals may be measured at various body parts, and since there is no need to add or replace an electrode to measure a biometric signal, an advantage may be provided in terms of cost. Also, since the sensor and the item of clothing may be washed, management thereof may be facilitated.

While exemplary embodiments have been shown and described above, it will be apparent to those skilled in the art that modifications and variations could be made without departing from the scope of the present invention as defined by the appended claims.

What is claimed is:

1. A sensor for measuring biometric information, the sensor comprising:
   a biometric electrode sensing biometric information in a state in which the biometric electrode is in contact with a surface of the skin; and
   a signal line transmitting the sensed biometric information,
   wherein the biometric electrode was formed by printing a mixture solution, obtained by mixing a carbon nanotube (CNT) dispersion with textile paint, on an inner surface of the item of clothing that comes into contact with a human body, and
   wherein the CNT dispersion was prepared by mixing 3.0wt. % of CNT and an isopropyl alcohol (IPA) solvent, by being stirred by a stirrer for 0.5 to 4 hours, by being aged for 24 hours, and a supernatant was subsequently removed using a centrifugal separator.

2. The sensor of claim 1, wherein the signal line is formed by printing the mixture solution on an inner surface of the item of clothing.

3. The sensor of claim 2, wherein the textile paint is printed on a surface of the signal line.

4. The sensor of claim 1, further comprising:
   a snap button provided at an end portion of the signal line; and
   a signal processing device having a detachable recess formed to be attached to or detached from the snap button, and receiving biometric information transmitted through the signal line.

5. The sensor of claim 4, wherein the signal processing device includes:
   an amplifier amplifying the received biometric information;
   a filter filtering the amplified biometric information; and
   a communications module wirelessly transmitting the filtered biometric information outwardly.

6. An item of clothing comprising:
   a sensor for measuring biometric information including a biometric electrode sensing biometric information in a state in which the biometric electrode is in contact with a surface of the skin and a signal line transmitting the sensed biometric information,
   wherein the biometric electrode was formed by printing a mixture solution, obtained by mixing a carbon nanotube (CNT) dispersion with textile paint, on an inner surface of the item of clothing that comes into contact with a human body, and
   wherein the CNT dispersion was prepared by mixing 3.0wt. % of CNT and an isopropyl alcohol (IPA) solvent, by being stirred by stirrer for 0.5 to 4 hours, by being aged for 24 hours, and a supernatant was subsequently removed using a centrifudal separator.

7. The item of clothing of claim 6, wherein the signal line is formed by printing the mixture solution on an inner surface of the item of clothing.

8. The item of clothing of claim 7, wherein the textile paint is printed on a surface of the signal line.

9. The item of clothing of claim 6, wherein the sensor further includes:
   a snap button provided at an end portion of the signal line; and
   a signal processing device having a detachable recess formed to be attached to or detached from the snap button, and receiving biometric information transmitted through the signal line.

10. The item of clothing of claim 9, wherein the signal processing device includes:
    an amplifier amplifying the received biometric information;
    a filter filtering the amplified biometric information; and
    a communications module wirelessly transmitting the filtered biometric information outwardly.

11. The item of clothing of claim 6, wherein the item of clothing is formed of a material having elasticity.

* * * * *